United States Patent [19]

Brown

[11] Patent Number: 5,618,544
[45] Date of Patent: Apr. 8, 1997

[54] METHOD OF DECREASING CUTANEOUS SENESCENCE

[75] Inventor: Gregory L. Brown, Louisville, Ky.

[73] Assignee: Bays-Brown Dermatologics, Inc., Louisville, Ky.

[21] Appl. No.: 287,340

[22] Filed: Aug. 8, 1994

Related U.S. Application Data

[63] Continuation-in-part of Ser. No. 103,398, Aug. 6, 1993, abandoned, which is a continuation-in-part of Ser. No. 928,264, Aug. 12, 1992, abandoned.

[51] Int. Cl.$^6$ .................................................. A61K 37/66
[52] U.S. Cl. ........................................... 424/401; 530/399
[58] Field of Search .................................. 514/8, 12, 21; 424/401; 530/399

[56] References Cited

U.S. PATENT DOCUMENTS

| | | | |
|---|---|---|---|
| 4,533,635 | 8/1985 | Saglier et al. | 435/240 |
| 4,604,234 | 8/1986 | Fuiji et al. | 514/2 |
| 4,670,257 | 6/1987 | Saglier et al. | 426/95 |
| 4,808,402 | 2/1989 | Leibovich et al. | 424/423 |
| 4,832,946 | 5/1989 | Green | 424/70 |
| 4,839,164 | 6/1989 | Smith | 424/64 |
| 4,843,063 | 6/1989 | Seyedin et al. | 514/2 |
| 4,929,442 | 5/1990 | Powell | 424/85.2 |
| 4,959,353 | 9/1990 | Brown et al. | 514/12 |
| 5,023,090 | 6/1991 | Levin | 424/520 |
| 5,064,655 | 11/1991 | Uster et al. | 424/450 |
| 5,104,977 | 4/1992 | Sporn et al. | 530/399 |
| 5,130,298 | 7/1992 | Cini et al. | 514/12 |
| 5,219,998 | 6/1993 | Levin et al. | 530/388.24 |

FOREIGN PATENT DOCUMENTS

| | | |
|---|---|---|
| 444638 | 9/1991 | European Pat. Off. . |
| 2654342 | 5/1991 | France . |
| 91/18999 | 12/1991 | WIPO . |

OTHER PUBLICATIONS

PN JP5043442A–Abstract: Skin Cosmetic Material Contains a Basic Fibroblast Growth Factor Prevent Skin Age, Hayashibara et al., 1993.
Derwent Ab: 104, 1986: 104:192928u; 104:173476h; 116:241736p; 106182467v; 117:219741k; 115:176096t.
Derwent abstract for JP 5,043,442.
Chemical Abstracts 10422:19298u for JP 6,105,006.
Chemical Abstracts 10622:182467v for JP 6,219511.
Chemical Abstracts 10420:174376h for JP 6,115,810.
Chemical Abstracts 11624:241736p for JP 429.916.
Chemical Abstracts 11722:219741k for JP 4,145,100.
Chemical Abstracts 11517:176096t for *Fragrance,* 19(7):99–102 (1991).
Kawammoto et al. "Transforming growth factor type beta stimulates epidermal growth factor–dependent cell growth of in vivo and in vitro senescent human skin fibroblast." *Cell Structure Functions* (1988) 13(6):616.
Hollenberg et al., "Receptors for insulin and epidermal growth factor–urogastrone in adult human fibroblasts do not change with donor age," *Mech. Ageing Dev.* 11(1) (Aug. 1979).
Allen, Sir G., "Cosmetics—chemical technology or biotechnology?" *International J. Cos. Sci.* 6(12) (Apr. 1984).
Chua et al., "Receptor for epidermal growth factor retains normal structure and function in aging cells," *Mech. Ageing Dev.* 34(1):35–55 (Mar. 1986).
Brown et al., "Enhancement of wound Healing by Epidermal Growth Factor: An Initial Clinical Report," *New England Journal of Medicine,* 321:76–79 (1989).
Brown et al., "Stimulation of Healing of Chronic Wounds by Epidermal Growth Factor," *Plastic & Reconstructive Surgery,* 88:189 (1991).
Brown et al., "Acceleration of Tensile Strength of Incisions Treated with EGF and TGF–beta," *Annals of Surgery,* 208(6) 788–794 (1988).

Primary Examiner—Thurman K. Page
Assistant Examiner—Sharon Howard
Attorney, Agent, or Firm—Gladys H. Monroy, Esq.

[57] ABSTRACT

The appearance of human skin is improved, e.g., epidermal cell, and thereby cutaneous senescence is decreased, by topically administering to human skin an effective amount of a composition comprising a mixture of protein growth factors consisting essentially of (a) epidermal growth factor (EGF) and (b) a member selected from the group consisting of transforming growth factor-alpha (TGF-α), fibroblast growth factor (FGF) and a mixture of transforming growth factor-alpha (TGF-α) and fibroblast growth factor (FGF), in a cosmetically acceptable carrier.

21 Claims, No Drawings

METHOD OF DECREASING CUTANEOUS SENESCENCE

CROSS-REFERENCE TO RELATED APPLICATIONS

This application is a continuation-in-part of U.S. Ser. No. 08/103,398, filed Aug. 6, 1993, abandoned, which is a continuation-in-part of U.S. Ser. No. 07/928,264, filed Aug. 12, 1992, abandoned. This application also claims priority to PCT/US93/07470. The disclosures of the above mentioned U.S. and PCT applications are incorporated herein by reference.

TECHNICAL FIELD

The invention relates to a cosmetic composition and a method to improve the appearance of human skin and thereby the stigmata of aging.

BACKGROUND OF RELATED ART

It is well known that as individuals age the rate of epidermal cell replication and desquamation, i.e. turnover of cells, decreases or the epidermis becomes senescent, this frequently produces a dull, aged appearance. In addition, the vascularity of skin decreases with time and the underlying collagenous framework undergoes structural fragmentation secondary to aging and photo-damage, hence elastosis; as a result, wrinkles and sagging occur.

"Senescence" at the cellular level results from inadequate DNA repair leading to disordered and/or nonexistent cell replication. Loss of mitotic control factors in the nucleus and cytoplasm including disordered nuclear cytoplasmic exchange and permanent closing of microcirculatory capillary beds results in focal cell dropout and loss of cell and organelle membrane function.

The lifetime effects of the damage include wrinkling and hardening of the skin with age. The skin is made up of supportive material, including elastin and collagen. Collagen is a major protein component of the white fibers of connective tissue, such as cartilage and bone. White elastin is the major protein in the connective tissue of large blood vessels in the skin which enables these tissues to stretch and resume their original confirmation. Both collagen and elastin contain fibers that are linked together with imide bonds. It is believed that mammalian or human aging involves the oxidation of imide bonds to amide bonds with decreased elastic and flexible properties. A free radical mechanism is involved in wrinkling of the skin and results from the negative effects oxidation products which causes tissue aging.

A prospective randomized double blinded clinical trial using skin graft donor sites to determine whether recombinant epidermal growth factor (EGF) would accelerate the rate of epidermal cell regeneration in humans was conducted as described in Brown, et al., "Enhancement of Wound Healing by Epidermal Growth Factor: An Initial Clinical Report," *New England Journal of Medicine*, 321:76–79 (1989). Epidermal growth factor (EGF) was evaluated for its effect on topical treatment of healing chronic wounds in a prospective open label cross over trial as described in Brown, et al., "Stimulation of Healing of Chronic Wounds by Epidermal Growth Factor," *Plastic & Reconstructive Surgery*, 88:189 (1991).

U.S. Pat. No. 4,695,590 describes a method for retarding aging by administering synthetic chemicals, such as certain hydroxy diphenyl alkyl derivatives, preferably by oral administration. It would be desirable to avoid the internal administration of synthetic chemicals both for convenience and to avoid possible side effects of internally administered synthetic chemicals.

A variety of protein factors are known to be essential to the growth and differentiation of cells including epidermal cells. Many of these proteins extracted from tissues have been identified: such as epidermal growth factor (EGF), insulin-like growth factor (IGF), platelet-derived growth factor (PDGF), fibroblast growth factor (FGF) and the like. U.S. Pat. No. 4,959,353 describes the use of epidermal growth factor for treating corneal wounds and U.S. Pat. No. 5,130,298 describes compositions of epidermal growth factor stabilized against degradation with metal cations and used for treating wounds. U.S. Pat. No. 5,104,977 discloses use of TGF-beta with either TGF-alpha for treating damaged tissue. However, as these patents illustrate, protein growth factors have not been previously shown to decrease epidermal cell senescence in unabraded or nonwounded skin. It had been previously thought that large proteins such as growth factors could not penetrate uninjured or intact skin in order to reach the appropriate basal cell layers to increase cellular replication and thereby decrease epidermal cell senescence.

It would be desirable to have a simple method to decrease epidermal cell and thereby cutaneous senescence in humans with or without aesthetic and reconstructive surgery.

SUMMARY OF THE INVENTION

The invention is directed to a method for improving the appearance of the human skin and thereby decreasing the stigmata of aging in humans by topically administering to human skin a composition comprising a mixture of protein growth factors consisting essentially of (a) epidermal growth factor (EGF) and (b) a member selected from the group consisting of transforming growth factor-alpha (TGF-α), and fibroblast growth factor (FGF) and a mixture of transforming growth factor-alpha (TGF-α) and fibroblast growth factor (FGF) in a topical cosmetically acceptable carrier, in an amount that effectively to improve the appearance of the human skin, e.g., by decreasing cutaneous senescence in humans.

It previously has been doubted that such growth factor proteins could reach the appropriate basal cell layer to produce increased cellular mitosis and hence replication. By contrast, use of the composition and method of the invention results in one or more affects such as decreased senescence of epidermal cells thereby increasing the rate of cellular replication and desquamation producing a more youthful appearance; delaying cutaneous atrophy, the thinning of epidermis and dermis and the increase of hydroxyproline content of the dermis.

DETAILED DESCRIPTION OF THE INVENTION

Unless defined otherwise herein, all technical and scientific terms used herein have the same meaning as commonly understood by one of ordinary skill in the art to which this invention is directed. Although any methods and materials similar or equivalent to those described herein can be used in the practice or testing of this invention, the preferred methods and materials are now described hereinafter. For convenience, the following definitions are also provided for use in describing the invention.

DEFINITIONS

As used herein, "epidermal cells" means the outer epithelial portion of the skin, i.e. cuticle.

As used herein, "cutaneous" is synonymous with the skin.

As used herein, "skin" means the membrane covering of a human body. The layers of the skin are the epidermis and the dermis.

As used herein "epidermal cell or cutaneous senescence" means the state of growing old and particularly damage to the epidermal cells of human skin which results from partial damage or complete destruction of the cells, conversion of imide bonds to amide bonds in collagen and/or elastin caused by toxic byproducts of oxygen metabolism, free-radical pathology mechanisms or by photo-damage and generalized aging.

Thus, decreasing epidermal cell and thereby cutaneous senescence in a human means reducing or inhibiting senescence, including one or more affects such as reversing photo-damage or other regenerative effects, such as increasing underlying skin vascularity, increasing the rate of cellular replication and desquamation producing a more youthful appearance, increasing collagen synthesis and homogeneity, delaying cutaneous atrophy and thinning of epidermis and dermis, and the like. While not being bound by any theory, it is also believed that the method of the invention results in decreased elastosis, increasing underlying vascularity, increasing collagen synthesis and structural homogeneity and reversing photo-damage.

As used herein, "effective amount to decrease senescence" means the amount of protein growth factor or composition thereof in a topical cosmetically acceptable carrier which is applied to human skin to achieve the desired result e.g., decrease cutaneous senescence in a human.

As used herein "flow cytometric analysis" is a method of photon beam cellular detection which measures the percentage of the total skin cells in the actively dividing stage-called the S-phase. Flow cytometry can be used to establish whether a protein growth factor treatment of the invention increased the baseline cellular division rate of the treated skin.

As used herein "the protein growth factors" include both native and recombinant protein growth factors as well as biologically active fragments and analogs thereof capable of decreasing epidermal cell and thereby cutaneous senescence. These individual protein growth factors (epidermal growth factor (EGF), fibroblast growth factor (FGF) and transforming growth factor-alpha (TGF-α)) and fragments or analogs thereof are well known.

Preferred because of their availability and senescence decreasing properties are a mixture of EGF and FGF.

Although it can be desirable and may even be required by regulatory agencies, to apply a human protein growth factor to humans, it is not a requirement of the method. Thus, a protein growth factor having a human source can be administered to humans but also a protein growth factor having a non-human source, such as rat, bovine, canine and the like can be administered to humans.

Likewise, the tissue source of the protein growth factor is not critical and includes, but is not limited to, brain, pituitary, hypothalamus, chondrosarcoma, cartilage, placenta and the like. Preferably the tissue source is human tissue.

A particular benefit of the invention is a simple method of topical administration to the skin of a composition for decreasing epidermal cell senescence in a human which does not require the intact skin to have been pretreated to stimulate cell growth, particularly a simple method of topical administration to the skin not requiring abrading of the intact skin by a plastic surgery technique or wounding in any way.

However, in one preferred embodiment of the invention, the skin is pretreated to remove the stratum corneum. The pretreatment can be mechanical, such as abrading, for example, with lussa or the like, or the like or can be chemical, including biochemical, such as treatment with a keratolytic agent, such as alpha-hydroxy acid, or with a cosmetically acceptable oil.

Because a more youthful and pleasing appearance is the generally desired result of the method of the invention, the topical carrier is a topical cosmetically acceptable carrier. By "topical cosmetically acceptable carrier" as used herein is meant any substantially non-toxic carrier conventionally usable for topical administration of cosmetics in which the protein growth factor will remain stable and bioavailable when applied directly to the skin surface. For example, the protein growth factor can be dissolved in a liquid, dispersed or emulsified in a medium in a conventional manner to form a liquid preparation or is mixed with a semi-solid (gel) or solid carrier to form a paste, powder, ointment, cream, lotion or the like. Suitable cosmetically acceptable carriers are known to those of skill in the art and include cosmetically acceptable liquids, creams, oils, lotions, ointments, gels, or solids, such as conventional cosmetic night creams, foundation creams, suntan lotions, sunscreens, hand lotions, make-up and make-up bases, masks and the like. The compositions can contain other ingredients conventional in cosmetics including perfumes, estrogen, Vitamin A, C and E, alpha-hydroxy of alpha-keto acids such as pyruvic, lactic or glycolic acids, lanolin, vaseline, aloe vera, methyl or propyl paraben, pigments and the like.

Suitable topical cosmetically acceptable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, such as discussed below, alcohols, polyols, and the like. Preferably, because of its non-toxic topical prgperties, the carrier is a water miscible carrier composition that is substantially miscible in water. Such water miscible topical cosmetically acceptable carrier composition can include those made with one or more appropriate ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions, gels or the like.

In one embodiment of the invention, the topical cosmetically acceptable carrier comprises a sustained release or delayed release carrier. The carrier is any material capable of sustained or delayed release of the protein growth factor to provide a more efficient administration resulting in one or more of less frequent and/or decreased dosage of the protein growth factor, ease of handling, and extended or delayed effects on decreasing epidermal cell senescence. The carrier is capable of releasing the protein growth factor when exposed to any oily, fatty, waxy, or moist environment on the area being treated or by diffusing or by release dependent on the degree of loading of the factor to the carrier in order to obtain releases of the factor. Nonlimiting examples of such carriers include liposomes, microsponges, microspheres, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Preferably, the sustained or delayed release carrier is a liposome, microsponge, microsphere or gel.

The compositions used in the method of the invention are applied directly to the skin cell areas to be treated. While not required, it is desirable that the topical composition maintain the factor at the desired location for about 24 to 48 hours.

If desired, one or more additional ingredients conventionally found in topical cosmetic compositions can be included with the carrier: such as a moisturizer, humectants, odor modifier, buffer, pigment, preservative, vitamins such as A, C and E, emulsifier, dispersing agent, wetting agent, odor-modifying agent, gelling agents, stabilizer, propellant, anti-microbial agents, sunscreen, enzymes and the like. Those of skill in the art of topical cosmetic formulations can readily select the appropriate specific additional ingredients and amounts thereof. Suitable non-limiting examples of additional ingredients include super oxide dismutase, stearyl alcohol, isopropyl myristate, sorbitan monooleate, polyoxyethylene stearate, propylene glycol, water, alkali or alkaline earth lauryl sulfate, methylparaben, octyl dimethyl-p-amino benzoic acid (Padimate O), uric acid, reticulin, polymucosaccharides, hyaluronic acids, aloe vera, lecithin, polyoxyethylene sorbitan monooleate, Vitamin A or C, tocopherol (Vitamin E), alpha-hydroxy or alpha-keto acids such as pyruvic, lactic or glycolic acids, or any of the topical ingredients disclosed in U.S. Pat. Nos. 4,340,586, 4,695, 590, 4,959,353 or 5,130,298, each incorporated herein by reference.

The effective amount of the protein growth factor or protein growth factor in the compositions used to decrease epidermal cell senescence in a human can vary depending on such factors as condition of the skin (severity of senescence), age of the skin, the particular protein growth factor employed, the type of formulation and carrier ingredients used, frequency of administration, overall health of the individual subject being treated and the like. The precise amount for any particular individual use can be determined by those of skill in the cosmetic art taking into consideration these factors and the present disclosure. By way of nonlimiting example, when the mixture of protein growth factors is EGF and FGF, the mixture of protein growth factors is usually administered to humans at a daily dosage of from about 1 microgram per ml to about 0.1 microgram per ml. Preferably, the factor is administered in at least two doses and no more than six doses per day, or less when a sustained or delayed release form is used.

The compositions for topical administration usually contain from about 0.0001% to about 90% by weight of the mixture of protein growth factors compared to the total weight of the composition, preferably from about 0.5% to about 20% by weight of the mixture of protein growth factors to the total composition, and especially from about 2% to about 5% by weight of the mixture of protein growth factors to the total composition.

The mixture of protein growth factor is administered by applying a coating or layer of the mixture of protein growth factors composition thereof to the skin area desired to be treated. As a practical matter of convenience, the applied material is rubbed into the skin. Applications need not be rubbed into the skin and the layer or coating can be left on the skin overnight.

The above description of the methods and compositions of the invention are provided to illustrate the invention and should not be regarded as limiting it in any way. Variations by changing or modification or the substitution of equivalent materials will be apparent to those of skill in the art.

All patents and publications referred to herein are incorporated in their entirety by reference thereto in this specification.

EXAMPLES

The invention is illustrated by the following examples which should not be regarded as limiting the invention in any way.

Example 1

Twelve volunteer subjects were enrolled into a study to determine the effects of a topical protein growth factor containing cream on senescence of the skin. It had previously been shown that topical EGF in a cream vehicle when applied topically to intact skin would reverse the senescent cell cycle.

These volunteer subjects were treated topically with four different cream preparations. The test areas were divided into four regions each forearm two centimeters distal to the antecubital fossa and each arm two centimeters proximal to the antecubital fossa. Each of the test areas were randomized among the volunteers and treated accordingly:

A-cream alone

B-cream plus 0.1 mcg/ml epidermal growth factor

C-cream plus 0.1 mcg/ml of EGF plus 0.1 mcg/ml TGF-alpha

D-cream plus 0.1 mcg/ml TGF-alpha

Each test area was treated twice daily for 60 days. One milliliter of the respective cream was applied to each test area during the dosing. At the end of the 60 day period, respective photographs were obtained from each test site on each subject; in addition, 2 mm punch biopsies were obtained from each test area. These biopsies were incubated for twelve hours in a trypsin solution to separate epidermis from dermis. Once the epidermis was separated it was submitted for flow cytometric analysis to determine the percentage of keratinocytes in the S-Phase. The results are set forth in Table 1 below.

TABLE 1

| | Percentage Cells in S-Phase | | | | |
|---|---|---|---|---|---|
| | A | B | C | D | AGE |
| subject 1 | 2.5 | 9.8 | 12.2 | 11.1 | 48 |
| subject 2 | 1.9 | 14.3 | 18.0 | 12.7 | 64 |
| subject 3 | 4.0 | 7.2 | 9.4 | 7.6 | 41 |
| subject 4 | 3.3 | 10.9 | 14.4 | 9.7 | 50 |
| subject 5 | 4.8 | 6.4 | 8.9 | 5.7 | 39 |
| subject 6 | 1.3 | 11.1 | 13.4 | 8.7 | 69 |
| subject 7 | 3.3 | 6.5 | 10.1 | 5.2 | 34 |
| subject 8 | 2.2 | 7.8 | 12.2 | 4.3 | 55 |
| subject 9 | 3.7 | 8.8 | 11.1 | 8.0 | 44 |
| subject 10 | 5.3 | 9.2 | 10.0 | 7.5 | 33 |
| subject 11 | 2.2 | 12.4 | 16.9 | 11.8 | 68 |
| subject 12 | 5.1 | 9.6 | 14.8 | 8.2 | 38 |
| AVERAGE | 3.3 | 9.5 | 12.6 | 8.37 | 48.5 |

The data in Table 1 demonstrated that EGF alone and TGF-alpha alone increased the cellular division rates significantly over controls ($p=0.05$). The difference between the increases produced by EGF alone versus TGF alpha alone were similar and not statistically significant when compared to each other. EGF appeared to produce a slightly greater effect. When the two were used simultaneously their affects appear to be additive in that the mitogenic results were about the same as those of either growth factor used alone in reversing the senescent epidermal cell cycle.

Example 2

Fibroblast growth factor (basic) is known to have strong mitogenic effects on mesodermal structures. The purpose of this study was to determine if the addition of FGF to an ectodermal mitogen would result in a dermal effect as well as the reversal of epidermal senescence.

Twelve subjects were entered into a study to determine the quantitative and qualitative effects produced by EGF and FGF on intact skin. Each subject was treated topically with four different creams. The areas treated were 2 cm distal to the antecubital crease on each forearm and 2 cm proximal to the antecubital fossa on each arm. The respective areas were randomized topically for each subject for the following cream combinations:

Cream 1 vehicle alone

Cream 2 EGF 0.1 mcg/ml in vehicle

Cream 3 FGF 0.1 mcg/ml in vehicle

Cream 4 EGF plus FGF, each 0.1 mcg/ml in vehicle

Both growth factors were administered in concentrations of 0.1 mcg/ml. Each cream was applied to the respective area twice daily for a total of 60 days. At the end of this treatment period, a 2 mm punch biopsy was obtained from each treatment site.

The punch biopsies were incubated overnight in a 0.25% trypsin solution at 30 C so as to separate epidermis from dermis. The following day, the epidermis was mechanically separated from the dermis. The epidermis was placed in a nutrient media and subsequently analyzed by flow cytometric analysis for percentage of keratinocytes in the S-phase. The dermis was the analyzed for hydroxyproline content. The results are set forth in Table 2 below.

TABLE 2

| | Percentage Cells in S-Phase | | | | |
|---|---|---|---|---|---|
| | Cream 1 | Cream 2 | Cream 3 | Cream 4 | AGE |
| subject 1 | 1.2 | 9.9 | 1.4 | 8.8 | 62 |
| subject 2 | 4.0 | 10.2 | 3.5 | 11.1 | 44 |
| subject 3 | 3.4 | 12.6 | 2.9 | 13.1 | 51 |
| subject 4 | 5.0 | 8.7 | 4.4 | 8.1 | 36 |
| subject 5 | 1.8 | 15.7 | 1.9 | 14.0 | 62 |
| subject 6 | 3.4 | 8.6 | 4.1 | 7.75 | 52 |
| subject 7 | 6.1 | 11.8 | 5.0 | 10.0 | 44 |
| subject 8 | 7.1 | 10.9 | 5.9 | 9.3 | 32 |
| subject 9 | 5.0 | 13.9 | 3.9 | 11.7 | 39 |
| subject 10 | 1.4 | 9.8 | 2.3 | 8.8 | 60 |
| subject 11 | 3.7 | 14.9 | 6.2 | 12.5 | 46 |
| subject 12 | 7.8 | 15.0 | 6.4 | 17.2 | 36 |
| AVERAGE | 4.15 | 11.8 | 3.99 | 11.1 | 47 |

The data in Table 2 demonstrated that there was a statistically significant increase ($p=0.05$) in cellular division for those cutaneous areas treated with EGF as has been shown by previous studies. In addition, the treatment of FGF alone produced no significant change in mitotic rate of the epidermis. However, when EGF and FGF were combined in the same topical vehicle, the epidermal effects were similar to previous results of EGF alone.

In an effort to determine if a dermal affect was produced by the strong mesodermal effects of FGF, the dermis was further analyzed for hydroxyproline content as an indirect measure of cellular activity. The following Table 3 gives the results of hydroxyproline measurements on all four dermal samples from each subject where the control was given a baseline value of one (1.0) and all other measurements given as a percentage of the control.)

TABLE 3

| HYDROXYPROLINE CONTENT AS PERCENTAGE OF CONTROL | | | | |
|---|---|---|---|---|
| | Cream 1 | Cream 2 | Cream 3 | Cream 4 |
| subject 1 | 1.0 | 1.1 | 1.6 | 1.95 |
| subject 2 | 1.0 | 0.9 | 1.3 | 2.1 |
| subject 3 | 1.0 | 1.2 | 1.65 | 1.88 |
| subject 4 | 1.0 | 1.0 | 1.25 | 1.66 |
| subject 5 | 1.0 | 1.0 | 1.14 | 1.36 |
| subject 6 | 1.0 | 0.77 | 1.23 | 1.78 |
| subject 7 | 1.0 | 1.0 | 1.77 | 2.04 |
| subject 8 | 1.0 | 1.9 | 1.35 | 1.42 |
| subject 9 | 1.0 | 1.0 | 1.22 | 1.82 |
| subject 10 | 1.0 | 1.22 | 1.35 | 1.56 |
| subject 11 | 1.0 | 1.1 | 1.67 | 2.31 |
| subject 12 | 1.0 | 1.0 | 1.88 | 2.78 |
| AVERAGE | 1.0 | 0.924 | 1.45 | 1.8 |

The data in Table 3 demonstrated that by hydroxyproline assay EGF alone seems to exert no statistical effect on the dermis whereas FGF alone produces a 45% increase in the hydroxyproline content ($p=0.01$) and EGF plus FGF (despite the lack of apparent effect of EGF alone) produces an additive effect over an above FGF alone ($p=0.05$).

What is claimed is:

1. A method for decreasing cutaneous cell senescence in a human which comprises topically administering to human skin an amount of a composition that is effective to decrease senescence, the composition comprising in a topical cosmetically acceptable carrier (a) a mixture of protein growth factors consisting essentially of epidermal growth factor (EGF), and (b) a member selected from the group consisting of transforming growth factor-alpha (TGF-$\alpha$), fibroblast growth factor (FGF), and a combination of TGF-$\alpha$ and FGF.

2. A method according to claim 1 wherein said mixture of protein growth factors is EGF and TGF-$\alpha$.

3. A method according to claim 2 wherein said mixture of protein growth factors further includes FGF.

4. A method according to claim 1 wherein said mixture of protein growth factors is EGF and FGF.

5. A method according to claim 1 wherein said skin is intact.

6. A method according to claim 1 wherein said topical cosmetically acceptable carrier is a water-miscible carrier.

7. A method according to claim 1 wherein said carrier composition is comprised of a constitutent selected from the group consisting of water, petroleum jelly, petrolatum, mineral oil, vegetable oil, animal oil, wax, or a polymer.

8. A method according to claim 1 wherein the carrier is a sustained or delayed release carrier.

9. A method according to claim 1 wherein the skin is pretreated to remove the stratum corneum.

10. A method to reduce or delay cutaneous cell atrophy in a human which comprises topically administering to the human skin a composition comprising a topical cosmetically acceptable carrier and an effective amount of a mixture of protein growth factors, the mixture consisting essentially of (a) EGF, and (b) a member selected from the group consisting of TGF-α, FGF, and a combination of TGF-α and FGF.

11. A method to reduce or delay thinning of the epidermis and dermis in human skin which comprises topically administering to the human skin a composition comprising a topical cosmetically acceptable carrier and an effective amount of a mixture of protein growth factors, the mixture consisting essentially of (a) EGF, and (b) a member selected from the group consisting of TGF-α, FGF, and a combination of TGF-α and FGF.

12. A method to increase the hydroxyproline content of the dermis in human skin which comprises topically administering to the human skin a composition comprising a topical cosmetically acceptable carrier and an effective amount of a mixture of protein growth factors, the mixture consisting essentially of (a) EGF, and (b) a member selected from the group consisting of TGF-α, FGF, and a combination of TGF-α and FGF.

13. A cosmetic composition for decreasing cutaneous cell senescence in a human by topical administration to human skin, the composition comprising a topical cosmetically acceptable carrier and an effective amount of a mixture of protein growth factors, the mixture consisting essentially of (a) EGF, and (b) a member selected from the group consisting of TGF-α, FGF, and a combination of TGF-α and FGF.

14. A composition according to claim 13 wherein said mixture of protein growth factors is EGF and TGF-α.

15. A composition according to claim 14 wherein said mixture of protein growth factors further includes FGF.

16. A composition according to claim 13 wherein said mixture of protein growth factors is EGF and FGF.

17. A composition according to claim 13 wherein said topical cosmetically acceptable carrier is a water-miscible carrier.

18. A composition according to claim 17 wherein said topical cosmetically acceptable carrier is comprised of a constituent selected from the group consisting of water, petroleum jelly, petrolatum, mineral oil, vegetable oil, animal oil, wax, and a polymer.

19. The composition according to claim 18 wherein said water-miscible carrier is water, petroleum jelly, petrolatum, mineral oil, vegetable oil, animal oil, wax or a polymer.

20. A composition according to claim 13 wherein the carrier is a sustained or delayed release carrier.

21. The composition of claim 13 which further includes an alpha-hydroxy acid.

* * * * *